United States Patent [19]
Lundberg

[11] Patent Number: 6,132,393
[45] Date of Patent: Oct. 17, 2000

[54] LIMITED MOBILITY SHOULDER BRACE

[76] Inventor: Leslie C. Lundberg, 3705 N. 17th St., Carter Lake, Iowa 51510

[21] Appl. No.: 09/186,979

[22] Filed: Nov. 5, 1998

[51] Int. Cl.[7] ...................................................... A61F 5/00
[52] U.S. Cl. ............................................. 602/19; 128/869
[58] Field of Search ........................ 602/4, 5, 19, 60–62; 128/869, 874–876; 2/311–319

[56] References Cited

U.S. PATENT DOCUMENTS

| | | | |
|---|---|---|---|
| 5,163,450 | 11/1992 | Cadichon et al. | 128/874 |
| 5,413,552 | 5/1995 | Iwuala | 602/4 |
| 5,538,015 | 7/1996 | Paulson | 128/869 |
| 5,551,447 | 9/1996 | Hoffman et al. | 128/869 |
| 5,643,184 | 7/1997 | Toso | 602/19 |

*Primary Examiner*—Danton D. DeMille
*Assistant Examiner*—Denise M. Pothier
*Attorney, Agent, or Firm*—Hovey, Williams, Timmons & Collins

[57] ABSTRACT

A limited mobility shoulder brace limits abduction and external rotation of the shoulder to reduce the risk of dislocation and subluxation. However, the brace permits flexion, extension, horizontal adduction and horizontal abduction of the shoulder so as to facilitate the user's ability to effectively participate in most sporting activities. The brace includes an attachment assembly which is secured about the torso, and a connecting member that is secured about the arm and shiftably coupled with the assembly in such a manner that the assembly and member cooperatively provide the previously noted degrees of stabilization and mobility.

20 Claims, 3 Drawing Sheets

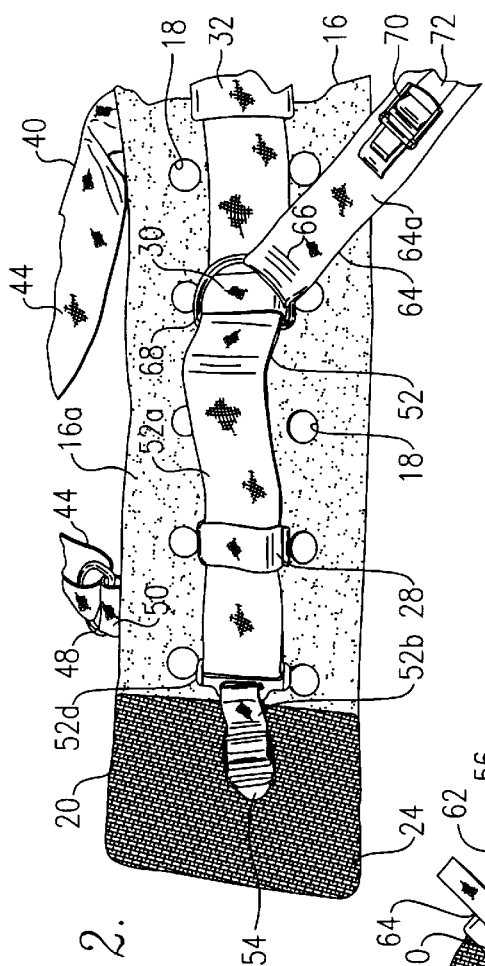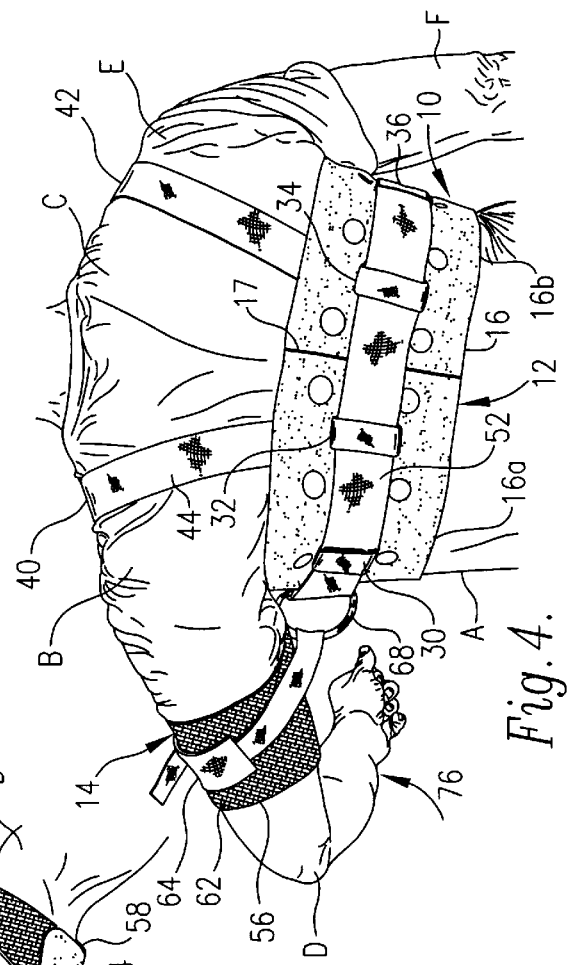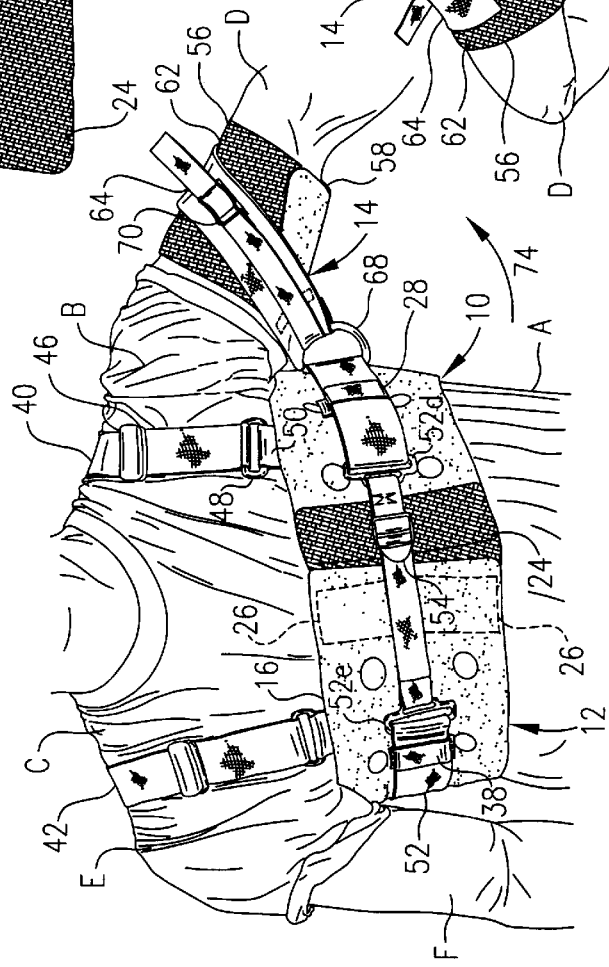

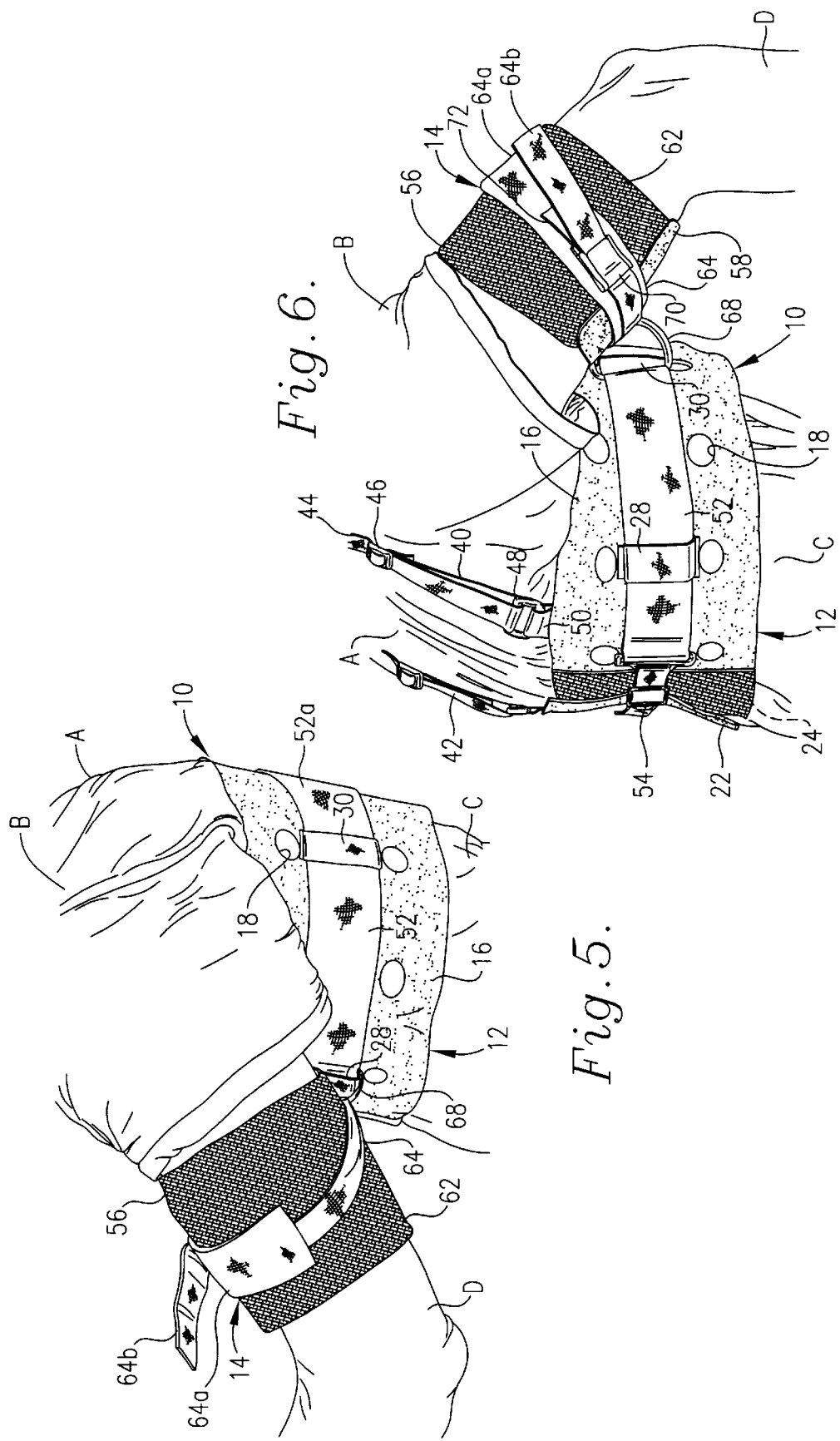

LIMITED MOBILITY SHOULDER BRACE

BACKGROUND OF THE INVENTION

1. Field of the Invention

The present invention relates generally to medical devices and sports equipment. More particularly, the present invention concerns an improved shoulder brace that limits abduction and external rotation of the shoulder yet permits the shoulder to extend, flex, horizontally adduct and horizontally abduct.

2. Discussion of Prior Art

One of the most common athletic injuries involves the shoulder. In particular, a significant number of amateur and professional athletes experience injuries that cause shoulder dislocation or subluxation. Those ordinarily skilled in the art will appreciate that nonsurgical treatment of a shoulder injury typically involves immobilization of the shoulder joint so as to permit healing of the surrounding soft tissue. In addition, such injuries tend to be chronic in nature, and steps must consequently often be taken to prevent recurring dislocation or subluxation during normal sports activity.

Those ordinarily skilled in the art will also appreciate that certain arm movements about the shoulder joint are more likely to cause dislocation or subluxation than others. For example, excessive shoulder abduction (generally vertical movement of the arm away from the midline of the body) and external rotation (various movements of the arm that cause outward twisting of the upper arm about its axis) are both likely to cause dislocation or subluxation of an injured shoulder. Moreover, an injured shoulder is particularly susceptible to dislocation and/or subluxation when these two types of movement are combined (e.g., when a baseball player winds up to throw the ball). On the other hand, some arm movements are highly unlikely to cause dislocation or subluxation after a shoulder injury. For example, flexion (generally forward swinging of the arm about the shoulder joint), extension (generally rearward swinging of the arm about the shoulder joint), horizontal adduction (generally horizontal movement of the arm toward the midline of the body), and horizontal abduction (generally horizontal movement of the arm away from the midline of the body) are all unlikely to cause dislocation or subluxation of the shoulder. It also noted that these types of movement facilitate and are normally associated with a number of shoulder movements used in a variety of sporting activities, such as running and skating (flexion and extension of the shoulder) or swinging of a racket or hockey stick ( horizontal adduction and horizontal abduction).

Conventional nonsurgical treatment typically involves placement of a brace on the body to at least partly immobilize the shoulder joint. In most instances, the arm associated with the injured shoulder is connected to the trunk of the body to limit movement of the shoulder. However, traditional braces tend to be overly restrictive, especially when the brace is being used as a preventative device simply to prevent recurring dislocation or subluxation. In other words, although traditional braces effectively prevent or limit movement that might cause shoulder dislocation and subluxation, they also prevent or limit movement that is not likely to cause dislocation or subluxation and that might be desirable during athletic activities. For example, a majority of conventional shoulder braces include an arm band or strap fixed to the torso, thereby limiting abduction and external rotation of the shoulder, but also preventing the shoulder from flexing, extending, horizontally abducting and horizontally adducting. These overly restrictive shoulder braces may consequently inhibit an athlete's involvement in a sport.

OBJECTS AND SUMMARY OF THE INVENTION

Responsive to these and other problems, an important object of the present invention is to provide a shoulder brace that effectively limits movement of the shoulder to reduce the risk of dislocation or subluxation, but does not overly restrict joint. In this respect, an important object of the present invention is to provide a shoulder brace that reduces the risk of shoulder dislocation or subluxation, yet permits participation in most sports activities. Particularly, an important object of the present invention is to provide a shoulder brace that limits abduction and external rotation of the shoulder, but permits the shoulder to flex, extend, horizontally adduct and horizontally abduct. It is also an object of the present invention to provide a shoulder brace having the foregoing objects, with the brace also having a simple, durable and inexpensive construction. In addition, it is an important object of the present invention to provide a shoulder brace that is comfortable, lightweight and that has exceptional ventilation.

In accordance with these and other objects evident from the following description ofthe preferred embodiment, the present invention concerns a shoulder brace including an attachment assembly configured to be secured to the torso. A connecting member configured to be secured to the arm is shiftably coupled with the attachment assembly in such a manner that the assembly and member cooperatively limit abduction and external rotation of the shoulder but permit flexion, extension, horizontal adduction and horizontal abduction of the shoulder. In this respect, the brace limits untoward shoulder movement which might cause shoulder dislocation or subluxation, yet permits shoulder movement that is critical to comfortable and effective participation in most sports activities.

In the preferred embodiment, the attachment assembly includes an elongated element having at least a portion thereof extending in a generally fore-and-aft direction along one side of the torso when the assembly is secured to the body, with the connecting member being slidably connected to the portion ofthe element. In providing the desired stability and mobility, the connecting member is preferably shiftable in a generally fore-and-aft direction along the portion of the element but generally restricted from shifting in a vertical direction relative to the portion of the element and from shifting in a lateral direction relative to the portion of the element.

Other aspects and advantages of the present invention will be apparent from the following detailed description of the preferred embodiment and the accompanying drawing figures.

BRIEF DESCRIPTION OF THE DRAWING FIGURES

A preferred embodiment of the invention is described in detail below with reference to the attached drawing figures, wherein:

FIG. 2 is an enlarged top elevational view of the shoulder brace, particularly illustrating the sliding attachment of the connecting member to the torso attachment assembly;

FIG. 3 is a front elevational view of the brace placed on a person, particularly illustrating the degree to which the brace limits shoulder abduction;

FIG. 4 is a rear elevational view of the brace placed on a person, particularly illustrating the degree to which the brace limits abduction and external rotation of the shoulder;

FIG. 5 is a left side elevational view of the brace placed on a person, particularly illustrating the manner in which the brace permits flexion of the shoulder; and FIG. 6 is a left side elevational view of the brace placed on a person, particularly illustrating the manner in which the brace permits extension of the shoulder.

DETAILED DESCRIPTION OF THE PREFERRED EMBODIMENT

Figure 1:
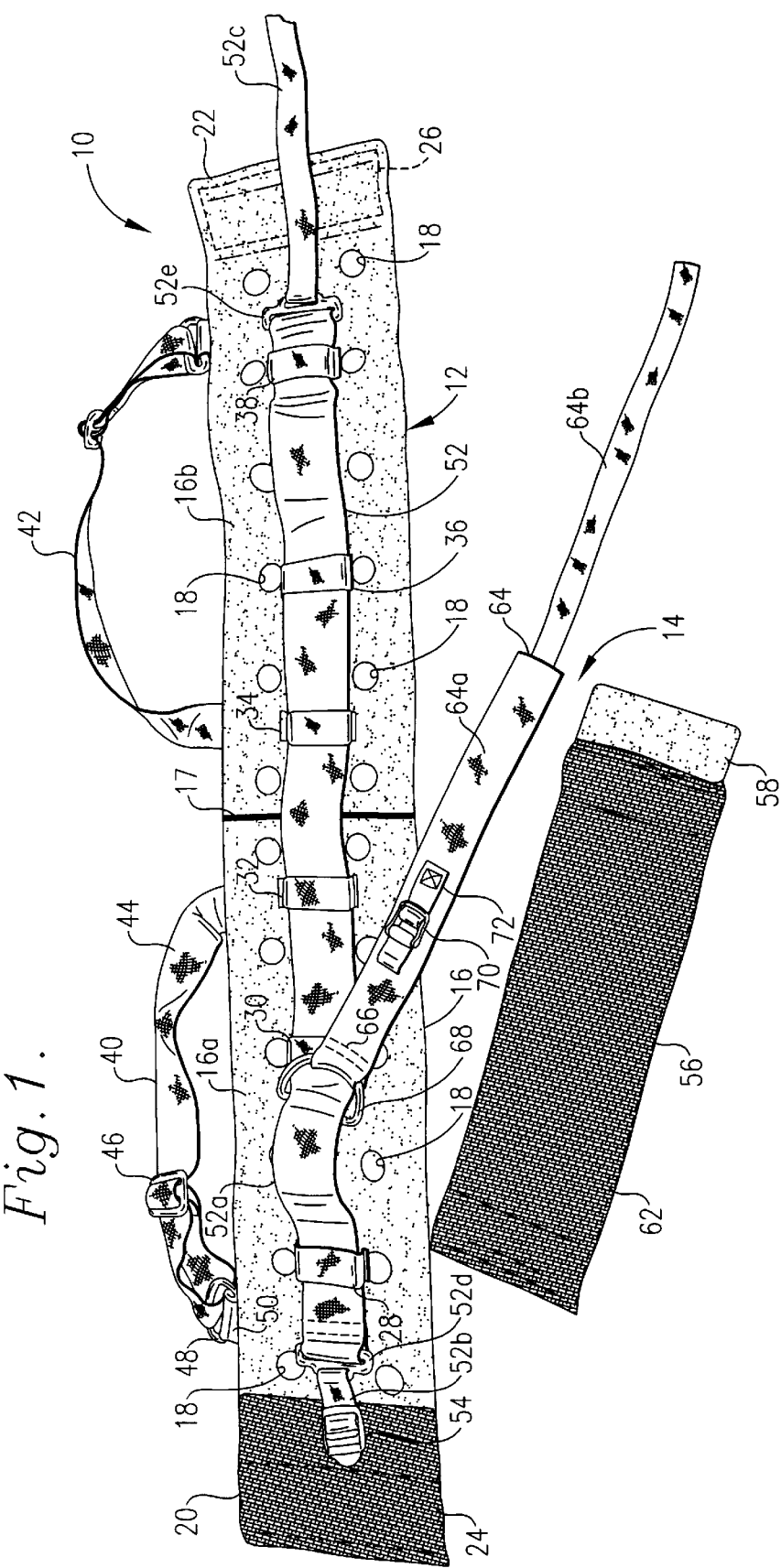
FIG. 1 is a top elevational view of a shoulder brace constructed in accordance with the principles ofthe present invention, particularly illustrating the brace removed from the body.

Turning initially to FIG. 3, the shoulder brace 10 selected for illustration is placed on the body A to stabilize the left shoulder B. The brace 10 is particularly effective in reducing the risk of shoulder dislocation or subluxation, while permitting limited mobility of the shoulder B. In the illustrated embodiment, the brace 10 is secured to the torso C and the left arm D for limiting movement of the arm D relative to the torso C in a manner that provides the desired degree of stability and mobility to the left shoulder B. However, the illustrated brace 10 may equally be used to treat the right shoulder E, with the brace 10 being similarly attached to the torso C and right arm F. In this respect, although the following description will involve the left shoulder B and arm D, it will be appreciated that the brace 10 may similarly be used to treat the right shoulder E. In fact, both shoulders B and E may be treated simultaneously, if desired.

The brace 10 generally includes a torso attachment assembly 12 which generally defines an anchor to which the arm D is connected when the brace 10 is worn. The brace further includes a connecting member 14 for connecting the arm D to the torso attachment assembly 12. As will be indicated below, the assembly 12 and member 14 are interconnected in a manner that restricts untoward shoulder movement yet permits desirable shoulder movement.

As perhaps best shown in FIG. 1, the attachment assembly 12 includes a flexible body wrap 16 preferably formed of an elasticized material such as a laminate of foam-type fabric and neoprene, although other suitable materials (e.g., a synthetic or natural cloth) may be used. The illustrated body wrap 16 consists of a two lengths 16a and 16b of the preferred material stitched to one another along a central seam 17 (see FIG. 1), with the assembled wrap 16 being dimensioned to extend around the upper torso of the user (see FIGS. 3–6). It will be noted that the wrap 16 includes a plurality of holes 18 that enhance ventilation and thereby the comfort of the brace 10 when it is worn. The wrap 16 is generally rectangular in shape and presents a pair of opposite end flaps 20 and 22 which are provided with complemental, adjustable fastening structure 24 and 26. In the illustrated embodiment, the structure 24 and 26 comprises hook-and-loop fastening material stitched to the flaps 20 and 22, although other suitable fastening devices (e.g., buttons, snaps, a belt and buckle, etc.) may be used.

For purposes which will subsequently be described, the wrap 16 includes a series of spaced apart belt loops 28,30, 32,34,36,38, each of which is preferably formed of a length of nylon webbing attached at its opposite ends by suitable stitching to the underlying material length 16a or 16b. It is noted that each of the fabric lengths 16a and 16b is provided with three respective belt loops 28,30,32 and 34,36,38. In addition, the loops associated with each fabric length are spaced generally the same distances from the seam 17 as the loops on the other fabric length.

The wrap 16 is secured about the torso C by wrapping the wrap 16 about the back of the upper torso (see FIG. 4) and fastening the end flaps 20 and 22 to one another in the front (see FIG. 3). If desired, the fastening structure 24 and 26 may be used to tightly secure the wrap 16 about the upper torso so that a compressive force is exerted against the body by the wrap 16. The adjustability of the fastening structure 24 and 26 permits this compressive force to be varied.

However, it is often times undesirable to exert a compressive force against the chest, as this may restrict breathing and create discomfort for the user. In this respect, the assembly 12 includes a pair of adjustable suspenders 40 and 42 projecting from the upper edge of the wrap 16 (see FIG. 1). The suspenders 40,42 are configured to extend over the torso C to prevent migration of the wrap 16 downwardly along the body. Thus, it is unnecessary to tightly secure the wrap 16 about the torso C for preventing movement of the wrap 16 out of the desired location.

The suspenders 40 and 42 are essentially identical in construction. Thus, it shall be sufficient to describe only the left suspender 40 in detail herein, with the understanding that the right suspender 42 is similarly constructed. The left suspender 40 includes a strap 44 attached to the fabric length 16a to project normally from the top edge of the wrap 16 in proximity to the seam 17. The strap 44 is preferably formed of nylon webbing, although other suitable materials (e.g., elasticized fabric, cloth, etc.) may be used. In the usual manner, the strap passes through a buckle 46, loops through a ring 48 attached to the wrap by a short strap 50, and then is fixed to the buckle 46. The overall length of the suspender 40 is consequently adjustable by sliding the buckle 46 along the strap 44. This provides, among other things, the ability to accommodate various body sizes.

As previously noted, the wrap 16 is provided with a series of belt loops 28–38 spaced along its length. The loops 28–38 are each configured to receive a belt 52 therein, with the belt 52 consequently being coupled to the wrap 16 by the loops 28–38. As perhaps best shown in FIG. 1, the belt 52 preferably includes a wide central section 52a and a pair of relatively narrow end sections 52b and 52c attached to opposite ends of the central section 52a by connectors 52d and 52e, respectively. The sections 52a,52b,52c of the belt are preferably formed of nylon webbing, although other suitable materials may be used. A buckle 54 is provided on the end section 52b for adjustably coupling with the end section 52c. Similar to the wrap 16, the belt 52 is dimensioned to extend around the torso C and may be securely fastened about the torso by intercoupling the end section 52c and buckle 54 (see FIG. 3). The adjustability of the belt 52 accommodates various torso sizes.

The illustrated connecting member 14 includes an upper arm band 56 formed of the same material as the wrap 16 and dimensioned to extend around the upper arm (see FIGS. 3–6). The band 56 is provided with suitable fastening structure for tightly securing the band about the arm. In the illustrated embodiment, the band 56 includes an end flap 58 having hook material (not shown) stitched to its underside, while the outer side of the remaining portion of the band 56 supports the complemental loop material 62 (see FIG. 1).

The connecting member 14 further includes a strap 64 preferably formed of the same material as the belt 52. The strap 64 includes a first section 64a and a relatively narrower second section 64b. The end of the first section 64a opposite from the second section 64b is formed into a loop by suitable stitching 66, with the loop loosely receiving a D-shaped ring 68 therein. Although not shown in the drawings, it will be appreciated that hook material is provided on the underside of the first section 64a so that the strap 64 may be removably attached to the arm band 56. A buckle 70 is supported on the outer side of the first section 64*a* by a nylon strip 72. As will be further described below, the second section 64*b* of the strap 64 is dimensioned to extend through the ring 68 and adjustably couple with the buckle 70 when the brace 10 is worn. Contrary to the first section 64*a*, the second section 64*b* preferably does not include hook fastening material along its underside. As perhaps best shown in FIG. 1, the illustrated arm band 56 and strap 64 are separate items removably attachable to one another. However, it is entirely within the ambit of the present invention to combine the band 56 and strap 64 into a single unitary element that is attached to the ring 68 and configured to be adjustably secured around the arm D.

In the illustrated embodiment, the connecting member 14 is shiftably coupled with the attachment assembly 12 as a result of the ring 68 being slidably received on the belt 52. In particular, the ring 68 is placed on the belt 52 between the loops 28 and 30 (see FIG. 2). This may be accomplished simply by pulling the left end of the belt out of the loop 28, sliding the ring 68 over the belt 52, and then reinserting the belt through the loop 28. It will be appreciated that the ring 68 serves as a fastener for fastening the strap 64 to the belt 52 in the desired manner. As shown in FIGS. 5 and 6, the loops 28 and 30 define stops that limit movement of the ring 68 along the belt 52. That is to say, the ring 68 is limited to movement along the portion of the belt located between the loops 28 and 30. In addition, the wrap 16 is dimensioned so that the loops 28 and 30 are located generally at the front and back margins of the left side of the torso C when the brace 10 is worn. Accordingly, the portion of the belt 52 located between the loops 28 and 30 extends in a generally horizontal, fore-and-aft direction along the left side of the torso C. This portion of the belt 52 consequently defines an elongated element along which the ring 68 can slide. It is also noted that the ring 68 is limited to movement along the length of the belt 52. That is to say, with the belt 52 secured about the torso C, the ring 68 is generally prevented from shifting vertically relative to the torso C and from shifting laterally relative to the torso C. Consequently, the remaining portion (i.e, the arm band 56 and strap 64) of the connecting member 14 is likewise permitted to move in a generally fore-and-aft direction and substantially prevented from moving in a vertical and lateral direction relative to the torso C. However, the arm D may be permitted to move vertically or laterally in a limited amount depending upon the slack provided in the strap 64 between arm band 56 and ring 68, as will subsequently be described.

It will be appreciated that the principles of the present invention are equally applicable to other variously constructed elongated elements along which the ring 68 can slide. For example, the wrap 16 may alternatively support a short metal or plastic bar (not shown) along the side of the torso, with the ring 68 being slidably received on the bar. Alternatively, a relatively short strap (not shown) may have its opposite ends stitched to the wrap 16 at generally the same locations as the loops 28 and 30, and the D-ring may be slidably received on the strap. Yet another alternative involves eliminating the wrap 16 and suspenders 40,42 and providing only the belt 52 along which the ring 68 can slide. It is also noted that the construction of the ring 68 may be varied to correspond with the structure along which the ring slides.

In use, the brace 10 is placed on the body A in the manner noted hereinabove. Particularly, the arms D and F are inserted through the suspenders 40 and 42 and the wrap 16 is secured about the torso C. The suspenders 40,42 may be adjusted, if necessary, and the belt 52 is fastened about the torso and tightened as needed. The arm band 56 is tightly secured about the left arm D, and the strap 64 is then attached to the arm band 56 simply by placing the first section 64*a* of the strap on the outwardly facing loop material 62 of the band 56. It is noted that the degree of abduction and external rotation of the shoulder B permitted by the brace 10 may be varied by the user. For example, in treating a recent shoulder injury, it may be desirable to prevent virtually all abduction and external rotation of the shoulder B. This may be accomplished by tightly securing the strap 64 to the arm band 56 while the arm D is against the torso C, such that there is virtually no slack in the strap 64 between the arm band 56 and ring 68. In such a configuration, the arm D will be generally limited to swinging movement against the torso C. On the other hand, if the brace 10 is being used only as a preventative device for reducing the risk of recurring dislocation or subluxation, the shoulder may be slightly abducted (i.e., the arm D may be swung away from the midline of the body) when the strap 64 is attached to the arm band 56. This will provide slack in the strap 64 between the arm band 56 and the ring 68 so as to permit slight abduction and external rotation when the brace 10 is worn. The attachment of the strap 64 to the arm band 56 is enhanced by wrapping the second section 64*b* of the strap 64 through the ring 68 and coupling the section 64*b* with the buckle 70, as shown in FIGS. 3–6.

As noted above, the belt 52 generally prevents laterally outward and vertical shifting of the ring 68, which limits swinging of the arm D away from the torso C and thereby abduction of the shoulder B. Such movement of the shoulder B is represented by the arrow 74 shown in FIG. 3. In the illustrated embodiment, the strap 64 has been attached to the arm band 56 in a manner that permits slight abduction (see FIGS. 3 and 4), although the degree of permitted abduction may be ffurther restricted as previously indicated. In addition, when the shoulder B is externally rotated (such movement being represented by the arrow 76 in FIG. 4), the arm band 56 moves with the upper arm and the strap 64 consequently pulls the ring 68 in a generally lateral direction away from the torso C. Again, such movement of the ring 68 is generally restricted by the belt 52. In the illustrated embodiment, the strap 64 is attached to the arm band 56 in a manner that permits some external rotation (see FIG. 4), although such movement of the shoulder B may be further restricted as previously indicated. Moreover, because the ring 68 is slidable along the portion of the belt 52 extending across the left side of the torso C, the arm D may be swung in a generally fore-and-aft direction. Particularly, the shoulder may be flexed until the ring 68 engages the loop 28, as shown in FIG. 5, and may be extended until the ring 68 engages the loop 30, as shown in FIG. 6. It will be appreciated that the brace 10 similarly permits horizontal adduction and horizontal abduction of the shoulder B. Particularly, as the shoulder B is horizontally adducted, the ring 68 slides forwardly along the belt 52, with the loop 28 serving to limit such movement. On the other hand, the ring 68 slides rearwardly along the belt 52 when the shoulder B is horizontally abducted, until the loop 30 is engaged. It is also noted that the illustrated loops 28 and 30 are positioned on the wrap 16 so as to permit virtually the entire normal range offlexion, extension, horizontal adduction and horizontal abduction of the shoulder B. However, the location of the loops 28 and 30 may be varied to provide different limitations to such movement.

In view of the foregoing, the brace 10 limits untoward shoulder movement which might cause dislocation or subluxation, yet permits shoulder movement that is useful in various sporting activities. As previously indicated, the brace 10 may similarly be used to treat the right shoulder E or both shoulders B and E simultaneously. With respect to the first alternative, it is again noted that the belt loops 36 and 38 are located along the right side of the torso C in locations corresponding to the points at which the belt loops 28 and 30 are located along the left side of the torso C. The D-shaped ring 68 may consequently be placed on the portion ofthe belt 52 located between the loops 36 and 38 to treat the right shoulder E in the same manner as that described above with respect to the left shoulder B. In addition, the brace 10 may be provided with a pair of connecting members for simultaneously treating both shoulders B and E, with one of the connecting members being shiftably coupled to the belt 52 between the loops 28 and 30 and the other connecting member being shiftably coupled to the belt 52 between the loops 36 and 38. It may generally be said that the torso attachment assembly 12 and the connecting member 14 each include a nonelastic element that is generally fixed to the respective body part, with the elements being interconnected in a manner that limits abduction and external rotation of the shoulder but permits generally unrestricted flexion, extension, horizontal abduction and horizontal abduction of the shoulder. In the illustrated embodiment, the element of the torso attachment assembly 12 comprises the belt 52, while the preferred element of the connecting member 14 comprises the strap 64 and D-shaped ring 68. As previously indicated, it is entirely within the ambit of the present invention to alternatively configure either or both of the elements in any other suitable manner.

The preferred forms of the invention described above are to be used as illustration only, and should not be utilized in a limiting sense in interpreting the scope of the present invention. Obvious modifications to the exemplary embodiments, as hereinabove set forth, could be readily made by those skilled in the art without departing from the spirit of the present invention.

The inventor hereby states his intent to rely on the Doctrine of Equivalents to determine and assess the reasonably fair scope of the present invention as pertains to any apparatus not materially departing from but outside the literal scope of the invention as set forth in the following claims.

What is claimed is:

1. A shoulder brace comprising:

a torso attachmnent assembly including a first substantially nonelastic elongated element, with the torso attachment assembly being configured to generally fix the first element to the torso; and an arm connecting member including a second substantially nonelastic element, with the connecting member being configured to generally fix the second element to one of the arms, said second element being slidibly connected to the first element in such a manner that the attachment assembly and connecting member cooperatively limit abduction and external rotation of the shoulder but permit generally unrestricted flexion, extension, horizontal adduction and horizontal abduction of the shoulder when the assembly and member are secured to the body.

2. A shoulder brace as claimed in claim 1, said attachment asseimbly including a flexible wrap dimensioned to extend around the torso, said first elenment being coupled with the wrap.

3. A shoulder brace as claimed in claim 2, said attachment assembly including a pair of adjustable suspenders attached to the wrap and configured to extend over the torso when the wrap is placed about the torso.

4. A shoulder brace as claimed in claim 2, said first element comprising an adjustable belt coupled with the wrap and dimensioned to extend around the torso.

5. A shoulder brace as claimed in claim 4, said wrap including a plurality of spaced apart belt loops, each of which toosely receives the belt therein, said second element being slidable coupled to the belt between a pair of said belt loops, with said pair of belt loops defining stops that limit sliding movement of said second element along the belt.

6. A sboulder brace as claimed in claim 1, said first element having at least a portion thereof extending in a generally fore-and-aft direction along one side of the torso when the assembly is secured to the body, said second element being slidably received on said portion of the first element.

7. A shoulder brace as claimed in claim 6, said first element comprising an adjustable belt dimensioned to extend around the torso.

8. A shoulder brace as claimed in claim 6, said second element including a ring slidably received on said portion of the first element.

9. A shoulder brace as claimed in claim 8, said connecting member including an arm band dimensioned to extend around the arm, said second element including a flexible strap connected to the ring and removably attachable to the arm hard.

10. A shoulder brace comprising:

a torso attachment assembly configured to be secured to the torso of a human body: and a connecting member configured to be secured to one of the arms of the body, said connecting member being shiftably coupled with the attachment assembly in such a manner that the attachment assembly and connecting member cooperatively limit abduction and external rotation of the shoulder but permit shoulder to flex, extend, horizontally adduct and horizontally abduct when the assembly and member are secured to the body, said attachment assembly including an elongated element having at least a portion thereof extending in a generally fore-and-aft direction along one side of the torso when the assembly is secured to the body, said connecting member being slidably received on said portion of the element, said connecting member including a ring slidablv received on said portion of the elongated element, said connecting member including an arm band dimensioned to extend around the arm, and a flexible strap connected to the ring and removably attachable to the arm band, said strap presenting opposite first and second end sections, with said ring being connected to the first end section, said strap including a buckle attached to the first end section, said second end section being dimensioned to loop through the ring and adjustably couple to the buckle when the attachment assembly and connecting member are secured on the body.

11. A shoulder brace comprising:

a torso attachment assembly configured to be secured to the torso of a human body; and a connecting member including a substantially non-elastic strap and a fastener with the connecting member being configured to fix the strap to one of the arms of the body, said fastener being slidable attached to the attachment assembly such that the fastener is limited to sliding movement in a fore-and-aft direction relative to the attachment assembly and the arm is thereby permitted to shift in a generally fore-and-aft direction relative to the attachment assembly and is substantially prevented from shifting in a generally vertical direction relative to the attachment assembly and from shifting in a generally lateral direction relative to the attachment assembly, when the brace is worn.

12. A shoulder brace as claimed in claim 11, said attachment assembly including a flexible wrap dimensioned to extend around the torso.

13. A shoulder brace as claimed in claim 12, said attachment assembly including a pair of adjustable suspenders attached to the wrap and configured to extend over the torso when the wrap is placed about the torso.

14. A shoulder brace as claimed in claim 12, said attachment assembly including an adjustable belt coupled with the wrap and dimensioned to extend around the torso.

15. A shoulder brace as claimed in claim 14, said wrap including a plurality of spaced apart belt loops, each of which loosely receives the belt therein, said fastener being slidably coupled to the belt between a pair of said belt loops, with said pair of belt loops defining stops that limit sliding movement of said fastener along the belt.

16. A shoulder brace as claimed in claim 1, said attachment assembly including an elongated element having at least a portion thereof extending in a generally fore-and-aft direction along one side of the torso when the assembly is secured to the body, said fastener being slidably received on said portion of the element.

17. A shoulder brace as claimed in claim 16, said element comprising an adjustable belt dimensioned to extend around the torso.

18. A shoulder brace as claimed in claim 16, said fastener comprising a ring connected to the strap and slidably received on said portion of the elongated element.

19. A shoulder brace as claimed in claim 18, said connecting member including an arm band dimensioned to extend around the arm, said strap being, removably attachable to the arm band.

20. A shoulder brace comprising:

a torso attachment assembly configured to be secured to the torso of a human body; and a connecting member configured to be secured to one of the arms of the body said connecting member being coupled with the attachment assembly in such a manner that the connecting member is shiftable in a generally fore-and-aft direction relative to the attachment assembly and is substantially prevented from shifting in a generally vertical direction relative to the attachment assembly and from shifting in a generally lateral direction relative to the attachment assembly, when the brace is worn, said attachment assembly including an elongated element having at least a portion thereof extending in a generally fore-and-aft direction alone one side of the torso when the assembly is secured to the body, said connecting member being slidably received on said portion of the element, said connecting member including a ring slidably received on said portion of the elongated element, said connecting member including an arm band dimensioned to extend around the arm, and a flexible strap connected to the ring and removably attachable to the arm band, said strap presenting opposite first and second end sections, with said ring being connected to the first end section, said strap including a buckle attached to the first end section, said second end section being dimensioned to loop through the ring and adjustably couple to the buckle when the attachment assembly and connecting member are secured on the body.

* * * * *